US00PP28352P3

(12) United States Plant Patent
Chapman

(10) Patent No.: US PP28,352 P3
(45) Date of Patent: Aug. 29, 2017

(54) ***VIOLA* PLANT NAMED 'BONNY'**

(50) Latin Name: *Viola×hybrida*
Varietal Denomination: Bonny

(71) Applicant: Robert Chapman, Lincoln (GB)

(72) Inventor: Robert Chapman, Lincoln (GB)

( * ) Notice: Subject to any disclaimer, the term of this patent is extended or adjusted under 35 U.S.C. 154(b) by 16 days.

(21) Appl. No.: 14/998,508

(22) Filed: Jan. 14, 2016

(65) Prior Publication Data

US 2016/0212908 P1 Jul. 21, 2016

Related U.S. Application Data

(60) Provisional application No. 62/125,278, filed on Jan. 16, 2015.

(51) Int. Cl.
*A01H 5/02* (2006.01)

(52) U.S. Cl.
USPC ..... Plt./323

(58) Field of Classification Search
USPC ..... Plt./323
See application file for complete search history.

*Primary Examiner* — Susan McCormick Ewoldt
(74) *Attorney, Agent, or Firm* — Barbara Campbell; Bethany R. Roahrig; Cochran Freund & Young, LLC

(57) ABSTRACT

A new cultivar of *Viola* plant named 'Bonny' that is distinguishable by compact basally branching habit, medium to large single bicolored blooms consisting of two lavender-colored upper petals and two bright yellow lateral petals and one bright yellow lower petal, and flowers which are heavily pleasantly fragrant. 'Bonny' is hardy in USDA Zone 5 and blooms from early spring through fall.

2 Drawing Sheets

Genus and species: *Viola×hybrida.*
Variety denomination: 'Bonny'.

BACKGROUND OF THE NEW PLANT

The present invention comprises a new and distinct variety of *Viola*, botanically known as *Viola×hybrida* and hereinafter referred to by the variety name 'Bonny'. 'Bonny' originated and was selected from a large population of hybrid seedlings from an open-pollinated *Viola* breeding program which was started by the inventor in 2010. The breeding program was conducted in a greenhouse nursery in Lincoln, Lincolnshire, United Kingdom. The aims of the breeding program were to produce a series of new *Viola* varieties exhibiting a range of flower colors borne on vigorous plants which are highly scented.

In spring 2011, the inventor organized open-pollination using combinations of selected, unnamed and unreleased seedlings retained from previous breeding cycles. The male and female parents of 'Bonny' are unknown. Seeds were harvested in late summer 2011, sown and grown over winter as seedlings which flowered in spring 2012. 'Bonny' was selected by the inventor in spring 2012. The inventor selected 'Bonny' together with the inventor'co-pending varieties 'Amy' (U.S. Plant Ser. No. 14/998,506), 'Sunny Jim' (U.S. Plant Ser. No. 14/998,507), and 'Sweetheart' (U.S. Plant Ser. No. 14/998,505) for their close similarity in plant habit and flower size and in order to create a consistent and uniform series.

'Bonny' was first vegetatively propagated by the inventor in spring 2012 using asexual shoot cuttings. 'Bonny' has been found to reproduce true to type in successive generations of asexual propagation.

SUMMARY

The following traits have been repeatedly observed and represent the distinguishing characteristics of the new *Viola* cultivar named 'Bonny'. 'Bonny' has not been tested under all possible conditions and phenotypic differences may be observed with variations in environmental, climatic, and cultural conditions, however, without any variance in genotype.

The following are the most outstanding and distinguishing characteristics of this new variety when grown under normal horticultural practices in Lincoln, Lincolnshire, United Kingdom.

1. 'Bonny' exhibits a naturally basally self-branching plant habit.
2. The foliage mound of 'Bonny' is 10 cm in height and 15 cm in diameter in its first season of flowering.
3. 'Bonny' exhibits medium to large single, bi-colored blooms consisting of two lavender-colored upper petals and two bright yellow lateral petals and one bright yellow lower petal.
4. The flowers of 'Bonny' are 3.8 cm in diameter.
5. 'Bonny' blooms are heavily pleasantly fragrant.
6. 'Bonny' does not require vernalization to initiate flowers.
7. 'Bonny' blooms continually from spring until fall.
8. 'Bonny' is hardy to USDA Zone 5.

DESCRIPTION OF THE PHOTOGRAPHS

The new *Viola* plant 'Bonny' is illustrated by the accompanying photographs which show each plant's overall plant habit including form, foliage, and flowers. The photographs are of plants 10 weeks in age grown in outdoor conditions. The colors shown are as true as can be reasonably obtained by conventional photographic procedures. Both photographs were made from a plant which has been grown outdoors in Oxnard, Calif. No pinching or chemical growth regulators have been employed. The photographs were made using conventional techniques and although flower and foliage color may appear different from actual color due to light reflectance, they are as accurate as possible by conventional photography.

DESCRIPTION OF THE NEW VARIETY

Figure 1:
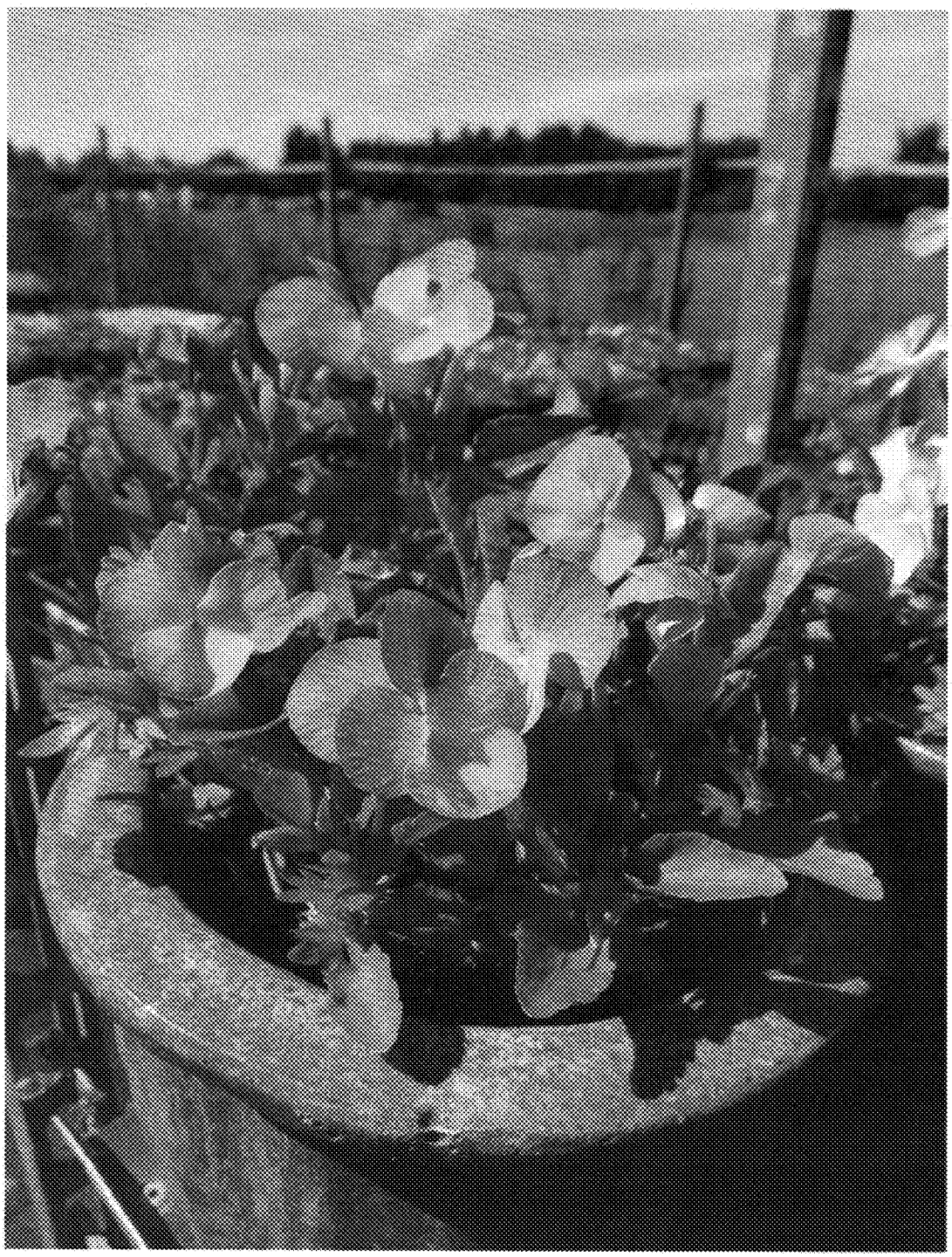
FIG. 1 shows a whole plant of 'Bonny' in flower.
Figure 2:
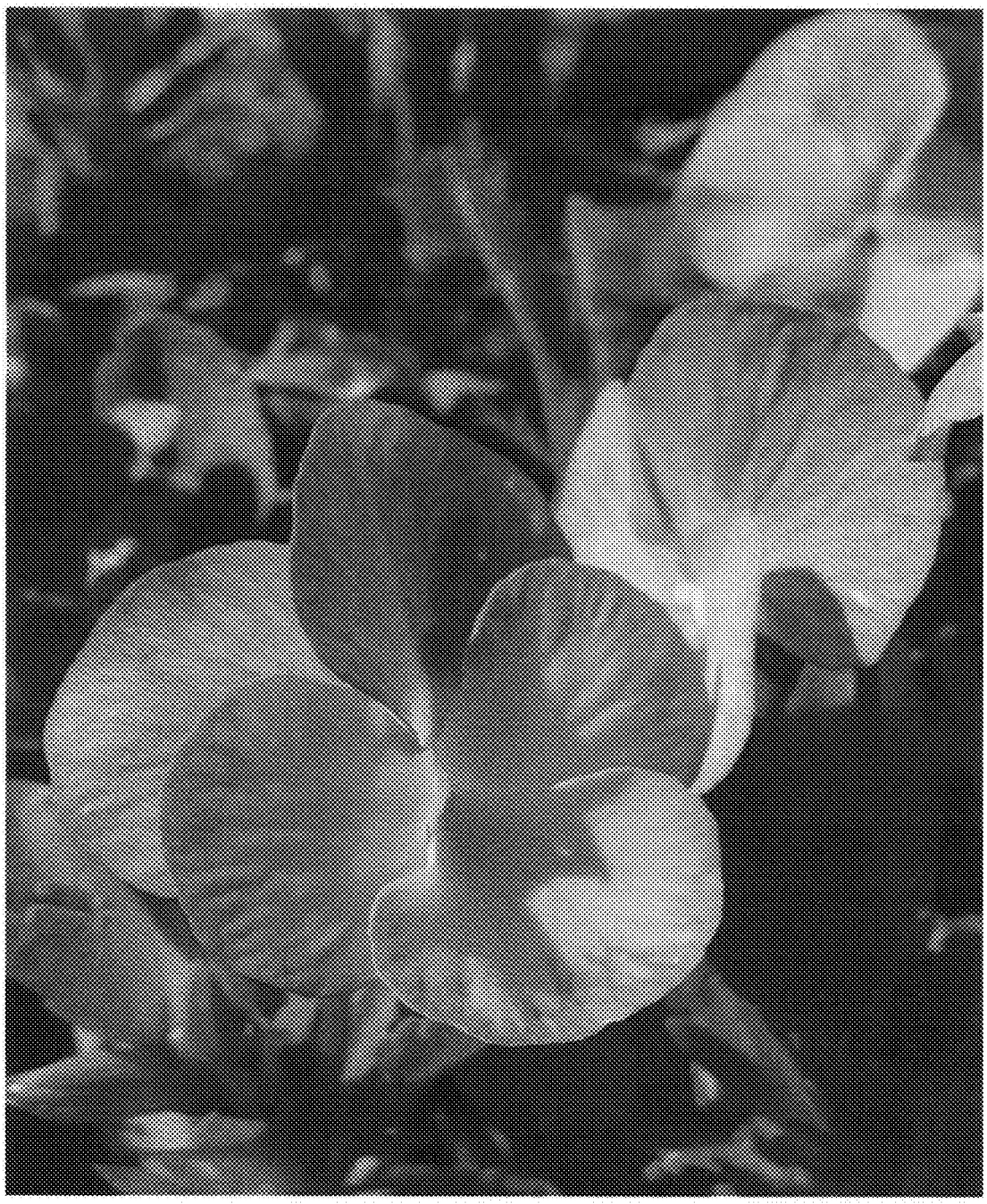
FIG. 2 depicts a close-up view of a flower on the plant shown in FIG. 1.

The following is a detailed botanical description of the new *Viola* cultivar named 'Bonny'. Observations and measurements were collected in September 2015 from 12-week-old plants which were growing in 1-gallon containers out of doors in Oxnard, Calif. Color determinations were made in accordance with the 2007 edition of The Royal Horticultural Society Colour Chart from London, England, except where general color terms of ordinary dictionary significance are used.

Botanical classification:

*Family*.—Violaceae.

*Genus*.—*Viola*.

*Species*.—×*hybrida*.

*Common name*.—Violet.

Plant:

*Habit*.—Compact.

*Type*.—Herbaceous perennial.

*Use*.—As planted containers and in the landscape.

*Propagation method*.—Shoot cuttings.

*Rooting system*.—Fine and fibrous.

*Vigor*.—Moderate.

*Time to develop roots* (*range*).—14 to 20 days to develop roots on an initial cutting.

*Temperature to develop roots*.—The recommended air temperature is 20-21° Centigrade.

*Crop time* (*range*).—Under spring and summer growing conditions, 'Bonny' will flower in a container after 10 weeks of growing from an unrooted cutting.

*Vernalization requirement for flowering*.—None.

*Plant dimensions*.—Foliage mound is 10 cm in height and 15 cm diameter. Flowers are borne at 10 cm to 15 cm above the foliage.

*Cultural requirements*.—Consistently moist soil or container medium.

*Pest or disease resistance or susceptibility*.—No particular disease or pest resistance or susceptibility is known to the inventor.

*Hardiness*.—USDA Zone 5.

Parentage: *Viola*×*hybrida* 'Bonny' is a hybrid seedling selection that resulted from the open-pollination of unknown parents.

Stem:

*Branching*.—Vigorously basally self-branching and spreading. 20 to 25 branch stems have been observed in the first growing season.

*Stem color*.—N144C.

*Stem length* (*average*).—8 cm to 10 cm.

*Stem diameter*.—0.3 cm.

*Stem shape*.—Cylindrical.

*Stem surface*.—Glabrous.

Foliage:

*Type*.—Evergreen.

*Leaf arrangement*.—Alternate.

*Leaf division*.—Simple.

*Leaf quantity*.—Approximately 12 to 16 per stem.

*Internode distance*.—0.75 cm to 1.0 cm.

*Margin*.—Crenate.

*Leaf shape*.—Ovate.

*Leaf length* (*range*).—2.0 cm to 3.5 cm.

*Leaf width* (*range*).—1.5 cm to 2.0 cm.

*Leaf color* (*abaxial surface*).—137C.

*Leaf color* (*adaxial surface*).—137A.

*Leaf base*.—Rounded.

*Leaf apex*.—Rounded.

*Venation*.—Pinnate.

*Vein color* (*abaxial and adaxial surfaces*).—137C.

*Leaf surface* (*abaxial and adaxial*).—Glabrous.

*Leaf attachment*.—Petiolate.

*Petiole color*.—138B.

*Petiole dimensions*.—0.5 cm to 1.0 cm in length and 1 mm in width.

*Petiole shape*.—Sulcate.

*Petiole surface*.—Glabrous.

Inflorescence:

*Inflorescence*.—Solitary terminal flower consisting of five petals.

*Inflorescence quantity* (*peak flowering*).—20 to 30 fully expanded flowers at one time.

*Aspect* (*range*).—Facing outward to pendant when aging.

*Inflorescence width*.—3.5 cm to 3.75 cm.

*Inflorescence height*.—4.0 cm.

*Inflorescence depth*.—2.0 cm.

*Inflorescence shape*.—Rotate.

*Blooming seasons*.—Early spring through fall.

*Inflorescence self-cleaning or persistent*.—Self-cleaning.

*Inflorescence fragrance*.—Pronounced fragrance, characteristic of the perfume of violets.

*Lastingness of inflorescence on the plant*.—5 to 7 days.

*Peduncle length* (*range*).—10 cm to 15 cm.

*Peduncle width*.—3 mm.

*Peduncle shape*.—Cylindrical.

*Peduncle surface*.—Glabrous.

*Peduncle color*.—144B.

*Peduncle strength*.—Stiff, wiry.

*Bud color*.—143C.

*Bud shape*.—Mostly cylindrical with rounded apex.

*Bud dimensions* (*average*).—1.30 cm in length and 0.40 cm in width.

*Bud surface*.—Glabrous.

*Corolla tube depth*.—6 mm.

*Petal quantity*.—5, consisting of 2 upper petals, 2 lateral petals, and 1 lower petal.

*Upper petals* (*two*).—Petal shape: Reniform. Petals fused or unfused: Unfused. Petal apex: Rounded. Petal base: Truncate to cuneate. Petal margin: Entire, lightly undulating. Petal length: 1.5 cm to 2.0 cm. Petal width: 2.0 cm to 2.5 cm. Petal color (both surfaces): Predominantly ranging between 92A and 92B; 3A towards petal bases. Petal surface (both surfaces): Glabrous.

*Lateral petals* (*two*).—Petal shape: Reniform. Petals fused or unfused: Fused. Petal apex: Rounded. Petal base: Truncate. Petal margin: Entire, lightly undulating. Petal length: 1.2 cm to 1.5 cm. Petal width: 1.5 cm to 1.8 cm. Petal color (both surfaces): Predominantly 3A; outer margins ranging between 92A and 92B. Petal surface (both surfaces): Glabrous.

*Lower petal* (*one*).—Petal shape: Obcordate. Petal apex: Emarginate. Fully developed petal exhibits broad notch at apex. Depth of notch: 0.3 cm. Petal base: Truncate. Petal margin: Entire, lightly undulating. Petal length: 1.5 cm to 1.7 cm. Petal width: 2.0 cm to 2.2 cm. Petal color (both surfaces): Predominantly 3A; outer margins and some veining 92B. Petal surface (both surfaces): Glabrous.

*Calyx shape*.—Stellate.

*Calyx diameter*.—2 cm.

*Sepals*.—5 in number.

*Sepal dimensions*.—1 cm in length and 0.40 cm in width.

*Fused or unfused*.—Sepals unfused.

*Sepal color* (*both surfaces*).—138A.

*Sepal apex*.—Acute.

*Sepal base*.—Truncate.

*Sepal surface*.—Glabrous.

*Sepal margin*.—Entire.

*Sepal shape*.—Lanceolate.

*Nectar spur*.—Characteristic of *Viola cornuta*. Protrudes through calyx, length 14 mm, diameter 1.5 mm.

*Spur color*.—8D, becoming 85B at apex.

*Spur apex shape*.—Rounded.

Reproductive organs:

*Stamen quantity*.—5 joined around ovary.

*Stamen length*.—4 mm.

*Stamen color*.—145D.

*Anther shape and dimensions*.—Ellipsoid, 3.5 mm in length, 2.0 mm in width.

*Anther color*.—164A.

*Pollen color*.—155C.

*Pollen quantity*.—Moderate.

*Pistil quantity*.—1.

*Pistil height*.—6.5 mm.

*Style height*.—1 mm.

*Style color*.—N144A.

*Stigma dimensions*.—Less than 1 mm in height and 1 mm in diameter.

*Stigma color*.—N144A.

*Stigma shape*.—Globular.

*Stigma surface*.—Glandular.

*Ovary position*.—Superior.

*Ovary color*.—N144A.

*Ovary shape*.—Dome-shaped.

*Ovary dimensions*.—6 mm in height and 3 mm in width.

Fruit and seed:

*Fruit*.—Trilocular capsule, length 8 mm to 10 mm, diameter 5 mm, color (mature) 162A. Capsule explodes to expose three boat-shaped valves, 6 mm in length, 3 mm in width.

*Seeds*.—Quantity ranges from 10 to 30 seeds per valve. Seed shape, dimensions and color: Globose, 1 mm in diameter, color 164A.

COMPARISON TO COMMERCIAL VARIETY

The inventor is not aware of any variety of *Viola*, whether produced from cuttings or from seed, which exhibits similar bi-colored flowers. In addition, the inventor selected 'Bonny' for the absence of prominent lower petal veining which is typical of many *Viola* varieties.

I claim:

1. A new and distinct cultivar of *Viola* plant named 'Bonny' as described and illustrated herein.

* * * * *